United States Patent [19]

White et al.

[11] Patent Number: 4,933,452

[45] Date of Patent: Jun. 12, 1990

[54] RADIATION SENSITIVE ISOCYANURATE COMPOUNDS

[76] Inventors: Nicholas J. White, 45 School Lane, Chapel Allerton, Leeds; Victor Kolodziejczyk, 6 Southcroft Avenue, Birkenshaw, Bradford, both of United Kingdom

[21] Appl. No.: 233,673

[22] Filed: Aug. 18, 1988

[30] Foreign Application Priority Data

Aug. 20, 1987 [GB] United Kingdom ............... 8719730

[51] Int. Cl.$^5$ .................. C07D 251/00; C08H 29/02; C08G 77/04

[52] U.S. Cl. ................... 544/204; 544/194; 525/79; 525/111; 525/154; 525/157; 525/191; 525/480; 528/254

[58] Field of Search ............... 544/204, 194; 525/73, 525/79, 111, 157, 154, 191, 480; 528/254

[56] References Cited

U.S. PATENT DOCUMENTS 4,350,753  9/1982  Shelnut et al. ............ 430/190
4,659,821  4/1987  Fauss et al. ............... 544/194

FOREIGN PATENT DOCUMENTS 0078980  5/1983  European Pat. Off. ....... 544/194
2851641  5/1979  Fed. Rep. of Germany .... 544/194

OTHER PUBLICATIONS

Kohler et al., J. Am. Chem. Soc. 49, 3181–3189 (1927).

*Primary Examiner*—Richard A. Schwartz
*Assistant Examiner*—J. Richter
*Attorney, Agent, or Firm*—Reed Smith Shaw & McClay

[57] ABSTRACT

A radiation sensitive compound and method for making same. The compound has the general formula:

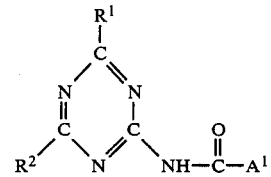

wherein, $R^1$ and $R^2$, which may be the same or different, each represents lower alkyl, aryl, X, $CHX_2$, $CH_2X$, $CX_3$ or $NHR^3$ wherein $R^3$ represents hydrogen, lower alkyl, aryl or

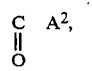

and provided at least one of $R^1$ and $R^2$ is $CX_3$, X is halogen, and $A^1$ and $A^2$ are each residues of $A^1$—H and $A^2$—H respectively wherein $A^1$—H and $A^2$—H which may be the same or different are each compounds containing at least one group having an active hydrogen atom. The method comprises reacting together an isocyanate of the formula

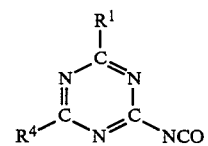

with a compound of the formula $A^1$—H or $A^2$—H to obtain the desired compound wherein $R^1$ or $R^4$ represents lower alkyl, aryl, X, $CHX_2$, $CX_3$, NCO or $NHR^5$ wherein $R^5$ represents hydrogen, lower alkyl or aryl and at least one of $R^1$ and $R^4$ is $CX_3$.

6 Claims, No Drawings

RADIATION SENSITIVE ISOCYANURATE COMPOUNDS

This invention relates to radiation sensitive compounds and more particularly, but not exclusively, is concerned with radiation sensitive compounds for use in the manufacture of radiation sensitive plates for lithographic printing plate production.

Radiation sensitive plates comprising a substrate coated with a radiation sensitive composition are well known in the production of lithographic printing plates and similar compositions are used for other purposes such as photoresists.

In use, the composition is image-wise exposed to radiation so that parts of the composition are struck by the radiation and parts are not. The radiation and non-radiation struck parts have differing solubilities in developer liquids and thus the more soluble parts can be selectively removed by application of such a liquid.

Radiation sensitive compositions comprising a photopolymerisable material and an initiator are well known. Halogen containing triazines, when irradiated with actinic radiation of suitable wavelength, are known to release a halogen radical which is capable of causing free radical polymerisation. In addition, the halogen radical can form free acid. Such compounds have therefore, been used as photoinitiators or acid release agents in radiation sensitive compositions for, for example, photoresists or printing plate coatings.

It is an object of the present invention to provide novel compounds which have the property of producing a free radical when irradiated and which also have other valuable properties.

According to one aspect of the present invention there is provided a radiation sensitive compound having the formula

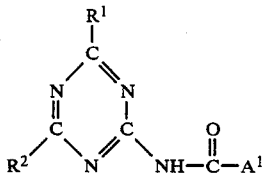

wherein $R^1$ and $R^2$, which may be the same or different, each represents lower alkyl, aryl, X, $CHX_2$, $CH_2X$, $CX_3$ or $NHR^3$ wherein $R^3$ represents hydrogen, lower alkyl, aryl or

and provided at least one of $R^1$ and $R^2$ is $CX_3$, X is halogen, and $A^1$ and $A^2$ are each residues of $A^1$—H and $A^2$—H respectively wherein $A^1$—H and $A^2$—H which may be the same or different, are each compounds containing at least one group having an active hydrogen atom.

According to another aspect of the present invention there is provided a method of producing a radiation sensitive compound having the formula

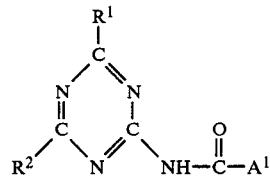

wherein $R^1$ and $R^2$, which may be the same or different, each represents lower alkyl, aryl, X, $CHX_2$, $CH_2X$, $CX_3$ or $NHR^3$ wherein $R^3$ represents hydrogen, lower alkyl, aryl or

provided at least one of $R^1$ and $R^2$ is $CX_3$, X is halogen and $A^1$ and $A^2$ are each residues of $A^1$—H and $A^2$—H respectively wherein $A^1$—H and $A^2$—H which may be the same or different, are each compounds containing at least one group having an active hydrogen atom; which method comprises the step of reacting together an isocyanate of the formula

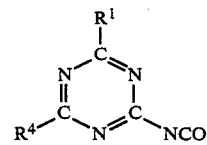

with a compound of the formula $A^1$—H or $A^2$—H to obtain the desired compound wherein $R^1$ or $R^4$ represents lower alkyl, aryl, X, $CHX_2$, $CH_2X$, $CX_3$, NCO or $NHR^5$ wherein $R^5$ represents hydrogen, lower alkyl or aryl and at least one of $R^1$ and $R^4$ is $CX_3$.

Preferably the group containing the active hydrogen atom is a OH, NH, SH or $CH_2$ group.

In the case where $R^1$, $R^2$ and/or $R^4$ are lower alkyl groups, they may contain from 1 to 4 carbon atoms.

In the case where $R^1$, $R^2$ and/or $R^4$ are aryl groups, they are preferably phenyl which may be substituted with halogen or alkyl or alkoxy containing 1-4 carbon atoms.

The compounds of the invention are capable of producing a free radical on irradiation and have other important properties which depend on the nature of the compound $A^1$—H or $A^2$—H containing the group having the active hydrogen atom.

The compounds according to the invention are particularly useful for use as a photoinitiator in radiation sensitive compositions containing photopolymerisable materials such as ethylenically unsaturated monomers. In such compositions, polymerisation is caused by the free radicals produced by irradiation of the photoinitiator and one problem with such conventional compositions of this type is that the efficiency of the polymerisation is reduced due to the tendency of the photoinitiator to migrate out of the composition.

By using as compounds $A^1$—H or $A^2$—H, from which $A^1$ and $A^2$ are derived, polymeric or oligomeric compounds which contain at least one group (and preferably two or more groups) containing an active hydrogen atom, it is possible to anchor the radical producing moiety or moieties to a larger molecule and thus produce a photoinitiator which has less tendency for migration. Suitable compounds are, for example, polyethylene glycol, pentaerythritol and hexane-1,6-diol.

Similarly, it is possible to produce an initiator in which the radical producing moiety or moieties are an integral part of the polymeric or oligomeric backbone by a reacting diisocyanate (i.e. an isocyanate of the above formula in which $R^1$ or $R^4$ is also an NCO group) and a polymeric or oligomeric compound containing one or more groups containing an active hydrogen compound.

Radiation-sensitive compositions based on monomers also conventionally contain a support (binder) resin. By using a compound of the invention wherein the compound $A^1$—H or $A^2$—H from which $A^1$ or $A^2$ is derived is a polymer containing at least one group having an active hydrogen atom and which has appropriate support (binder) properties, the support resin and the photoinitiator are combined into a single compound, thus reducing the number of separate components of the composition as well as reducing migration. Suitable polymers for this purpose are: poly(vinyl acetals), styrene-allyl alcohol copolymers, acrylic co- or terpolymers containing hydroxy alkyl (meth)acrylates, novolak resins and poly(vinyl phenol).

An alternative way of reducing initiator migration is to use a compound of the invention wherein the compound $A^1$—H or $A^2$—H from which $A^1$ or $A^2$ is derived is a compound which contains at least one group having an active hydrogen atom and which is capable of free radical polymerisation. Suitable compounds in this respect are those containing ethylenic unsaturation for example (meth)acrylates, such as 2-hydroxyethyl methacrylate and pentaerythritol triacrylate. In this case, the photoinitiator and the ethylenically unsaturated compound to be polymerised are in one and the same molecule.

As is well known, it is desirable that radiation-sensitive compositions change colour upon irradiation. One way of achieving a colour change is to incorporate, within the composition, a pH sensitive dye and a compound capable of producing acid when irradiated i.e. an acid releasing agent. As mentioned above, halogen-triazines are such agents. Thus in radiation sensitive compositions based on ethylenically unsaturated monomers, the compounds of the invention can act as both acid release agents and as photoinitiators. In other negative-working compositions and positive-working compositions, the compounds of the invention can act as acid release agents. More particularly, in the case of positive-working compositions which, as is well known, are based on quinone diazide esters (as the radiation-sensitive component) and alkali soluble binder resins (particularly novolak resins), the compound $A^1$—H or $A^2$—H from which $A^1$ or $A^2$ is derived can be either the quinone diazide ester or the novolak resin, thus obviating the need for a separate acid releasing agent.

An alternative way of obtaining a colour change is to use a compound of the invention wherein the compound $A^1$—H or $A^2$—H from which $A^1$ or $A^2$ is derived is a pH sensitive dye containing at least one group having an active hydrogen atom. Suitable dyes are, for example:

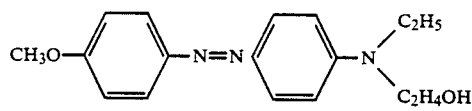

-continued

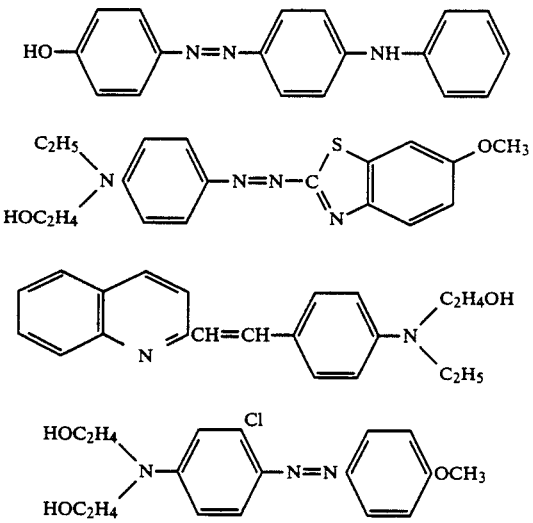

In this way, the invention provides a colour change system in a single molecule, and may also, if desired, be used to provide a polymeric or oligomeric dye.

The efficient production of the free radical on irradiation depends on the radiation having the correct wavelength to be absorbed by the initiator. However, a mismatch between the radiation wavelength and the initiator can be overcome by using a photosensitiser which absorbs at the wavelength of the radiation and then transfers the energy to the photoinitiator. This can be achieved by using a compound of the invention wherein the compound $A^1$—H or $A^2$—H from which $A_1$ or $A_2$ is derived is a compound which contains at least one group having an active hydrogen atom and which has photosensitising properties. Suitable compounds are for example:

4-hydroxybenzophenone; 7-hydroxy-4-methyl coumarin; 4-phenyl phenol; 2',4',5',7'-tetrabromo fluorescein (C.I. 453802); Thionin; 2-mercapto benzothiozole: 4-diethylamino-4'-(N-ethyl-N-hydroxyethyl)amino benzophenone; and 2(4(N-ethyl-N-hydroxyethyl)aminobenzylidene)inden-1-one.

In this way, it is possible to provide in a single compound, a sensitised initiator, which will absorb and be active at a specified wavelength.

According to a third aspect of the present invention there is provided a radiation sensitive compound having the formula:

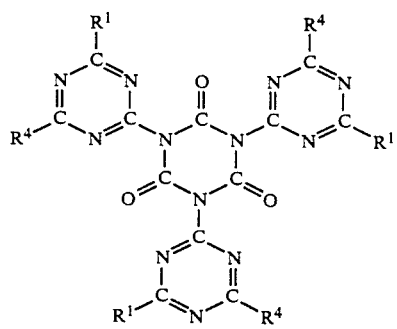

wherein $R^1$ and $R^4$ have the meanings given above.

Such compounds can be prepared by trimerising a compound having the formula:

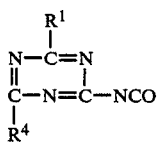

and may be used as photoinitiators and/or acid release agents in radiation sensitive compositions.

The following Examples illustrate the invention:

EXAMPLE 1

A solution in ethyl methyl ketone of a photopolymerisable composition comprising:
- 3 parts by weight of the dimethacrylate ester of the diglycidyl ether of bisphenol A,
- 1 part by weight of a vinyl acetate/crotonic acid copolymer,
- 0.43 parts by weight of compound I, and
- 0.15 parts by weight of ethyl Michler's ketone, was whirler coated onto a sheet of electrochemically grained and anodised aluminium and dried to form a radiation sensitive plate. The coating weight was 1.0 g per sq.m. The dried coating was overcoated with poly(vinyl alcohol) to prevent oxygen inhibition of the photopolymerisation reaction.

The radiation sensitive plate was exposed through a continuous tone Stouffer step wedge to ultraviolet light (20 mJ/cm$^2$ from a Berkey-Ascor printing down frame) and then developed with an aqueous solution containing sodium propanoate, sodium benzoate and a surfactant. The developed image of the resultant lithographic printing plate had a step wedge of solid 4, tail 10.

After storage under accelerated ageing conditions (30 degC., 95% relative humidity) for 3 weeks, analysis of the radiation sensitive coating of a similar plate showed that there had been negligible migration of Compound I. Exposure and development of the aged plate under the same conditions as above gave a similar step wedge reading of solid 4, tail 10.

PREPARATION OF COMPOUND I 3 g of PEG 600 (a polyethylene glycol) was dissolved in 20 mls N-methyl pyrrolidone (NMP) and to this solution was added 3.57 g of 2-isocyanato-4,6-bis(trichloromethyl)-s-triazine followed by 1 drop of dibutyl tin dilaurate. The reaction was then warmed to 40 degC. and held at 40 degC. for 3 hours. After this time the mixture was added to 100 mls water to stop the reaction, filtered and washed well with water. The product was dried under vacuum at room temperature.

COMPARATIVE EXAMPLE 1

Example 1 was repeated using, instead of Compound I, 0.15 parts by weight of [2-chloro-phenyl-4,6-bis(trichloromethyl)-s-triazine] as the photoinitiator. Exposure and development produced a step wedge reading of solid 4, tail 10.

After storage of a similar plate under the same accelerated ageing conditions as in Example 1 for 3 weeks, analysis showed a decrease of 33% in the original initiator content indicating that substantial migration had taken place. Moreover, exposure and development of the aged plate showed that it had become less sensitive, giving a solid 2, tail 7 step wedge.

EXAMPLE 2

Example 1 was repeated except that Compound II was used instead of Compound I. Similar results were obtained.

PREPARATION OF COMPOUND II 1.36g of pentaerythritol was added to 40 ml NMP and to this solution was added 101.4 g of 2-isocyanato-4-methyl-6-trichloromethyl-s-triazine followed by 1 drop of dibutyl tin dilaurate. The reaction was then warmed to 50° C. and held at this temperature for ten hours. The reaction was then stopped by adding the mixture to 200 ml water. The product was filtered out, washed well with water and dried under vacuum at room temperature.

EXAMPLE 3

Example 1 was repeated except that Compound III was used instead of Compound I. Similar results were again obtained.

PREPARATION OF COMPOUND III

Compound III was prepared by the same method as Compound II except that 0.88 g of N,N-dimethylene diamine and 5.07 g of the triazine were used.

EXAMPLE 4

Example 1 was again repeated except that Compound IV was used instead of Compound I. Similar results were again obtained.

PREPARATION OF COMPOUND IV 1.50 g of 1,6-hexane dithiol was added to 40 ml NMP and to this solution 2.81 g of 2,4-diisocyanato-6-trichloromethyl-s-triazine were added over a period of 30 minutes. The solution was stirred for an additional three hours at ambient temperature, added to 200 ml water to stop the reaction and filtered. The product was washed and dried under vacuum at room temperature.

EXAMPLE 5

A solution, in ethyl methyl ketone, of a photopolymerisable composition comprising:
- 3 parts by weight of the dimethacrylate ester of diglycidyl ether of bisphenol A,
- 1 part by weight of Compound V, and
- 0.15 parts by weight of ethyl Michler's ketone, was whirler coated onto a sheet of electrochemically grained and anodised aluminium and dried to form a radiation sensitive plate. The coating weight was 1.0 g per sq.m. The dried coating was overcoated with poly(vinyl alcohol) to prevent oxygen inhibition. The resultant radiation sensitive plate was exposed and developed as described in Example 1. A step wedge reading of solid 3, tail 9 was produced.

After storage for 3 weeks under the accelerated ageing conditions described in Example 1, a similar plate was exposed and developed. The sensitivity of the plate remained unchanged, as shown by a solid 3, tail 9 step wedge.

PREPARATION OF COMPOUND V 9.74 g of a modified poly(vinyl butyral) resin (containing 54 mol. % butyral, 26 mol. % hydroxy and 20 mol. % hydrogen phthalate ester) was dissolved in 50 mls NMP and to this solution was added 3.57g of 2-isocyanato-4,6-bis(trichloromethyl)-s-triazine followed by 1 drop of dibutyl tin dilaurate. The reaction was then warmed to 40 degC. and held at 40 degC. for 6 hours. After this time the mixture was poured into 300 mls water to stop the reaction, filtered and washed well with water. The product was dried at 35 degC. under vacuum.

EXAMPLE 6

Example 5 was repeated except that Compound VI was used instead of Compound V. Similar results were obtained.

PREPARATION OF COMPOUND VI 18.35 g of a poly(vinyl butyral) resin (containing 48 mol % butyral, 50 mol % hydroxy and 2 mol % acetate) was dissolved in 100 ml NMP and 13.79 g of p-toluene sulphonyl isocyanate. The mixture was held at ambient temperature for one hour and then 10.71 g of 2-isocyanato-4,6-bis(trichloromethyl)-s-triazine was added followed by 1 drop of dibutyl tin dilaurate. The mixture was then warmed to 40° C. and held at this temperature for six hours. The mixture was poured into water, filtered and the product was washed with water and dried under vacuum at 35° C.

EXAMPLE 7

Example 5 was repeated except that Compound VII was used in place of Compound V. Similar results were again obtained.

PREPARATION OF COMPOUND VII 15 g of a modified styrene/allyl alcohol copolymer (containing 70 mol % styrene, 15 mol % hydroxy and 15 mol % hydrogen phthalate ester) was dissolved in 75 ml NMP and then 5.07 of 2-isocyanato-4-methyl-6-(trichloromethyl)-s-triazine and 1 drop of dibutyl tin dilaurate were added. The mixture was then warmed to 50° C. and held at that temperature for ten hours. Finally the mixture was poured into 500 ml water, filtered and the product was washed with water and dried under vacuum at 35° C.

EXAMPLE 8

A positive working radiation sensitive coating solution comprising:
 6 parts by weight of a naphthoquinone diazide sulphonic acid ester,
 27 parts by weight of Compound VIII, and
 0.36 parts by weight of Sudan Yellow,
made up to 400 mls with a mixture of 95 parts acetone and 5 parts methyl oxitol was whirler coated onto electrochemically grained and anodised aluminium and dried at 100 degC. for 5 minutes to give a radiation sensitive plate with a coating weight of 2.5 g per sq.m.

The plate was exposed through a Stouffer step wedge to ultra-violet light (800 mJ/cm² from a Berkey-Ascor printing down frame) giving a yellow image against a red background. The plate was then dish-developed in 8% sodium metasilicate solution for 45 seconds, giving a step wedge reading of clear 2, solid 7.

After storage of the coating solution for 7 days at room temperature (20 degC.) analysis showed that negligible decomposition of Compound VIII had taken place. A radiation sensitive plate derived from the aged coating solution was exposed and showed equivalent contrast of the yellow image on the red background to a plate made from fresh coating solution.

PREPARATION OF COMPOUND VIII 10. 8g of cresol-novolak resin was dissolved in 50 mls NMP and to this solution was added 3.57 g of 2-isocyanato-4,6-bis(trichloromethyl)-s-triazine followed by 1 drop of dibutyl tin dilaurate. The reaction was completed and the product isolated as in Example 2.

COMPARATIVE EXAMPLE 8

Example 8 was repeated using 27 parts by weight of novolak resin and 0.44 parts by weight of 4-diazodiphenylamine tetrafluoroborate instead of Compound VIII. After exposure the contrast of the yellow image on the red background was similar as for the plate in Example 3, and, after development, gave a similar step wedge reading of clear 2, solid 7.

After storage of the coating solution for 7 days at room temperature, analysis showed that 10% of the original content of the 4-diazodiphenylamine tetrafluoroborate had decomposed. A radiation sensitive plate derived from the aged coating was exposed and the contrast of the yellow image on the red background was inferior to the contrast obtained in Example 8.

EXAMPLE 9

Example 8 was repeated except that the coating solution comprised:
 6 parts by weight of Compound IX
 27 parts by weight of cresol-novolak resin
 0.36 parts by weight of Sudan Yellow
Similar results were obtained.

PREPARATION OF COMPOUND IX 6.3 g of the bis ester of 2,3,4-trihydroxy benzophenone and naphthoquinone-(1,2)-diazide(2)-5-sulphonyl chloride was dissolved in 50 ml of 1,4-dioxan and 3.57 g of 2-isocyanato-4,6-bis (trichloromethyl)-s-triazine was added. The mixture was warmed to 35° C., maintained at that temperature for four hours and then poured into 500 ml water to stop the reaction. The product was filtered, washed with water and dried under vacuum at ambient temperature.

EXAMPLE 10

Example 1 was repeated adding 0.1 parts by weight of Compound X to the formulation as a colour change agent.

The resultant radiation sensitive plate was exposed through a step wedge to ultra-violet light (200 mJ/cm²) producing a red image on a yellow background. After development the red image retained its colour giving excellent contrast with the background, and a solid 6, tail 13 step wedge was obtained.

Visual inspection of a sample of the poly(vinyl alcohol) overcoat which had been removed prior to exposure indicated that a negligible amount of the Compound X had leached into the overcoat.

PREPARATION OF COMPOUND X 3.5g of a dye with the following structure:

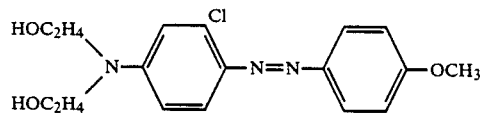

was dissolved in 20 mls NMP and to this solution was added 2.8 g of 2,4-diisocyanato-6-trichloromethyl-s-triazine followed by 1 drop of dibutyl tin dilaurate. The reaction was then warmed to 50 degC. and held at 50 degC. for 6 hours. After this time the mixture was added to 100mls water to stop the reaction, filtered and washed well with water. The product was dried under vacuum at room temperature.

COMPARATIVE EXAMPLE 10

Example 10 was repeated using 0.1 parts by weight of 3-chloro-4-(4'methoxyphenylazo)-N,N-bis(2"-hydroxyethyl)aniline instead of Compound X as the colour change agent.

The radiation plate was exposed as in Example 10 producing a red image on a yellow background. After development the red image became paler in colour resulting in a poorer contrast with the background than in Example 10.

Visual inspection of a removed sample of the poly(vinyl alcohol) overcoat prior to exposure revealed that it had a strong yellow colouration indicating that the colour change agent had leached into the overcoat.

EXAMPLE 11

Example 10 was repeated using Compound XI instead of Compound X. Similar results were obtained.

PREPARATION OF COMPOUND XI

Compound XI was prepared in a similar manner to Compound X except that 2.9 g of a dye having the structure

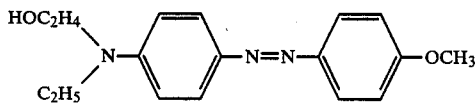

was reacted with 3.50 g of 2-(4'-chlorophenyl-4-isocyanato-6-trichloromethyl-s-triazine.

COMPARATIVE EXAMPLE 11

Comparative Example 10 was repeated except that the colour change agent used was 4-(4'-methoxyphenylazo)-N-ethyl-N-(2"-hydroxyethyl)-aniline.

The results were again similar.

EXAMPLE 12

Example 11 was repeated except that Compound XII was used instead of Compound XI. Similar results were obtained.

PREPARATION OF COMPOUND XII

Compound XII was prepared in a similar manner to Compound XI except that 2.83 g 2-N,N-(dimethylamino)-4-isocyanato-6-trichloromethyl-s-triazine was used.

EXAMPLE 13

A solution in ethyl methyl ketone of a photopolymerisable composition comprising:
3 parts by weight of Compound XIII,
1 part by weight of a vinyl acetate/crotonic acid copolymer and
0.15 parts by weight of ethyl Michler's ketone,
was whirler coated onto a sheet of electrochemically grained and anodised aluminium and dried to form a radiation sensitive plate. The coating weight was 1.0 g per sq.m.

The dried coating was overcoated with poly(vinyl alcohol) to prevent oxygen inhibition. The resultant radiation sensitive plate was exposed to radiation through a step wedge (200 mJ/cm$^2$ in a Berkey-Ascor frame) and developed as in Example 1. A step wedge reading of solid 5, tail 12 was produced.

PREPARATION OF COMPOUND XIII

To 4.84 g of 2-ethyl-2-hydroxy methyl)-1,3-propanediol diacrylate was added 2.8 g of 2,4-diisocyanato-6-trichloromethyl-s-triazine, 1 drop of dibutyl tin dilaurate and 0.01 g 4-methoxy phenol. This melt was then stored at 60 degC. for 10 hours to complete the reaction.

EXAMPLES 14–17

Example 13 was repeated using Compounds XIV-XVIII instead of Compound XIII.

PREPARATION OF COMPOUNDS XIV-XVII

These Compounds were prepared by dissolving appropriate amounts of various (meth)acrylate A-D as listed below in 150 ml of 1,4-dioxan, adding 14.05 g of 2,4-diisocyanato-6-trichloromethyl-s-triazine, heating the mixture to 50° C. and holding it at this temperature for 4 hours before evaporating the solvent at reduced pressure to isolate the product.

A=Pentaerythritol triacrylate (29.8 g)
B=Dipentaerythritol (monohydroxy) pentaacrylate (52.4 g)
C=Glycerol di(meth)acrylate (22.7 g)
D=Di-trimethylolpropane triacrylate (39.8 g)

EXAMPLE 18

Example 1 was repeated using 0.15 parts by weight of a Compound XVIII, instead of Compound I as the photoinitiator. A step wedge reading of solid 5, tail 12 was obtained.

After storage for 3 weeks under the accelerated ageing conditions described in Example 1, analysis of the coating showed that there had been negligible migration of Compound XVIII. Also, exposure and development of an aged plate showed that there had been no deterioration in the sensitivity of the radiation sensitive coating.

PREPARATION OF COMPOUND XVIII

This compound is the trimer of 2-isocyanato-4,6-bis(-trichloromethyl)-s-triazine and was produced by admixing 3.7 g of that compound, 4 g of epichlorohydrin and 1 drop of pyridine and stirring the mixture for nineteen hours at ambient temperature. The crude trimer (which has a chlorine content of 47.9% compared to the theoretical 59.7%) is isolated by evaporating the volatiles.

EXAMPLE 19

A solution in ethyl methyl ketone of a photopolymerisable composition comprising:
3 parts by weight of the dimethacrylate ester of the diglycidyl ether of bisphenol A,
1 part by weight of a vinyl acetate/crotonic acid copolymer and
0.3 parts by weight of Compound XIX
was whirler coated onto a sheet of electrochemically grained and anodised aluminium and dried to form a radiation sensitive plate. The coating weight was 1 g per sq.m. The dried coating was overcoated with poly(vinyl alcohol) to prevent oxygen inhibition.

The resultant radiation sensitive plate was exposed through a step wedge (20 mJ/cm$^2$ in a Berkey-Ascor frame) and developed as in Example 1. A step wedge reading of solid 2, tail 7 was produced.

PREPARATION OF COMPOUND XIX 1.98g of 4-hydroxy benzophenone was dissolved in 20 mls NMP and to this solution was added 3.57g of 2-isocyanato-4,6-bis(trichloromethyl)-s-triazine and 1 drop dibutyl tin dilaurate. The mixture was then heated to 50 degC. and held at 50 degC. for 6 hours. After this time the reaction mixture was poured into 100 mls water to stop the reaction, filtered and washed well with water. The product was dried under vacuum at room temperature.

EXAMPLES 20 and 21

Example 19 was repeated using Compounds XX and XXI in place of Compound XIX. Similar results were obtained.

PREPARATION OF COMPOUNDS XX and XXI

The compounds were produced in a similar manner to Compound XIX except that 1.76 g of 7-hydroxy-4-methyl coumarin and 1.67 g of 2-mercaptobenzothiazole were used instead of the 4-hydroxy benzophenone.

We claim:
1. A compound having the formula

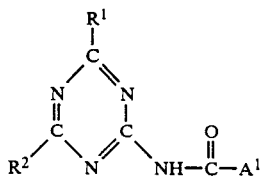

wherein $R^1$ and $R^2$, which may be the same or different, each represents lower alkyl, aryl, X, $CHX_2$, $CH_2X$, $CX_3$ or $NHR^3$ wherein $R_3$ represents hydrogen, lower alkyl, aryl or

and provided at least one of $R^1$ and $R^2$ is $CX_3$, X is halogen, and $A^1$ and $A^2$ are each derivatives of $A^1$—H and $A^2$—H respectively wherein $A^1$—H and $A^2$—H which may be the same or different, are each compounds containing at least one group having an active hydrogen atom, and said group having an active hydrogen atom is a —OH, —NH, —SH, or —CH$_2$— group.

2. A compound which is a trimer of an isocyanate having the formula

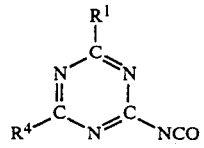

wherein $R^1$ or $R^4$ represents lower alkyl, aryl, X, $CHX_2$, $CH_2X$, $CX_3$, NCO or $NHR^5$ wherein $R^5$ represents hydrogen, lower alkyl or aryl and at least one of $R^1$ and $R^4$ is $CX_3$, and X is a halogen.

3. A compound having the formula

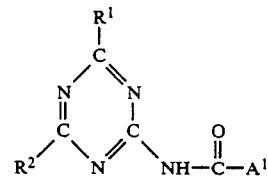

wherein $R^1$ and $R^2$, which may be the same or different, each represents lower alkyl, aryl, X, $CHX_2$, $CH_2X$, $CX_3$ or $NHR^3$ wherein $R^3$ represents hydrogen, lower alkyl, aryl or

and provided at least one of $R^1$ and $R^2$ is $CX_3$, X is halogen, and $A^1$ and $A^2$ are each derivatives of $A^1$—H and $A^2$—H respectively wherein $A^1$—H and $A^2$—H which may be the same or different, are each compounds containing at least one group having an active hydrogen atom, wherein each of said compounds containing at least one group having an active hydrogen atom has photosensitising properties and is selected from the group 4-hydroxybenzophenone, 7-hydroxy-4-methyl coumarin; 4-phenyl phenol; 2',4',5',7'-tetrabromo fluorescein; thionin, 2-mercapto benzothiozole; 4-diethylamino-4' (N-ethyl-N-hydroxyethyl) amino benzophenone; and 2(4(N-ethyl-N-hydroxethyl) aminobenzylidene)inden-1-one.

4. A compound as described in claim 1, wherein each of said compounds containing at least one group having an active hydrogen atom is polyethylene glycol, pentaerythritol, hexane diol, a polyvinyl acetal, a styrene-allyl alcohol copolymer, an acrylic copolymer or terpolymer containing a hydroxyalkyl acrylate or methacrylate, a novolak resin, a poly(vinyl phenol), an acrylate, methacrylate, 2-hydroxethyl methacrylate or pentaerythritol triacrylate.

5. A compound as described in claim 1, wherein each of said compounds containing at least one group having an active hydrogen atom is a pH sensitive dye.

6. A compound as described in claim 1, wherein each of said compounds containing at least one group having an active hydrogen atom has photosensitising properties.

* * * * *